United States Patent [19]
Hengl

[11] Patent Number: 5,884,346
[45] Date of Patent: Mar. 23, 1999

[54] DEVICE FOR THE RECOVERY AND STORAGE OF WASTE

[75] Inventor: Patrick Hengl, Montgiscard, France

[73] Assignee: Innovation-Ingeniere-Integration-Systeme, Montgiscard, France

[21] Appl. No.: 436,255

[22] PCT Filed: Nov. 13, 1993

[86] PCT No.: PCT/FR93/01107

§ 371 Date: May 15, 1995

§ 102(e) Date: May 15, 1995

[87] PCT Pub. No.: WO94/10893

PCT Pub. Date: May 26, 1994

[30] Foreign Application Priority Data

Nov. 13, 1992 [FR] France .................................. 9213917

[51] Int. Cl.$^6$ .................................................. A47K 11/00
[52] U.S. Cl. .................................................. 4/484; 53/576
[58] Field of Search ........................... 4/222, 482, 484, 4/449, 483; 53/170, 567, 576

[56] References Cited

U.S. PATENT DOCUMENTS

| | | | |
|---|---|---|---|
| 2,671,906 | 3/1954 | Potts | 4/484 |
| 3,452,368 | 7/1969 | Couper | 4/484 |
| 3,643,266 | 2/1972 | Black | 4/484 |
| 3,648,302 | 3/1972 | Winters | 4/484 |
| 3,693,193 | 9/1972 | May | 4/484 |
| 3,723,999 | 4/1973 | Miller | 4/484 |
| 3,908,336 | 9/1975 | Forslund | 53/576 |
| 4,519,104 | 5/1985 | Nilsson | 4/484 |

FOREIGN PATENT DOCUMENTS

| | | |
|---|---|---|
| 1804452 | 6/1969 | Germany . |
| 24 57 093 | 6/1975 | Germany . |
| 1294129 | 10/1972 | United Kingdom . |
| WO 88 02614 | 4/1988 | WIPO . |

Primary Examiner—Robert M. Fetsuga
Attorney, Agent, or Firm—Harold H. Dutton, Jr.

[57] ABSTRACT

Waste recovery device comprising a container (62) for receiving waste, a radially expansible sheath (19) which is disposed about the container (62) and forms a lining within it, a deflecting member (66, 67) arranged to incurve the path of the sheath (19), a mechanism (73–77, 80–82) for feeding the sheath (19) by holding it under tension so as to cause it to close once it contacts the deflecting member (66, 67), and by displacing as desired the sleeve (19) over a predefined distance so as to cause a new section of sleeve to pass into the container (62), and a mechanism (54) for actuating the feed mechanism.

29 Claims, 11 Drawing Sheets

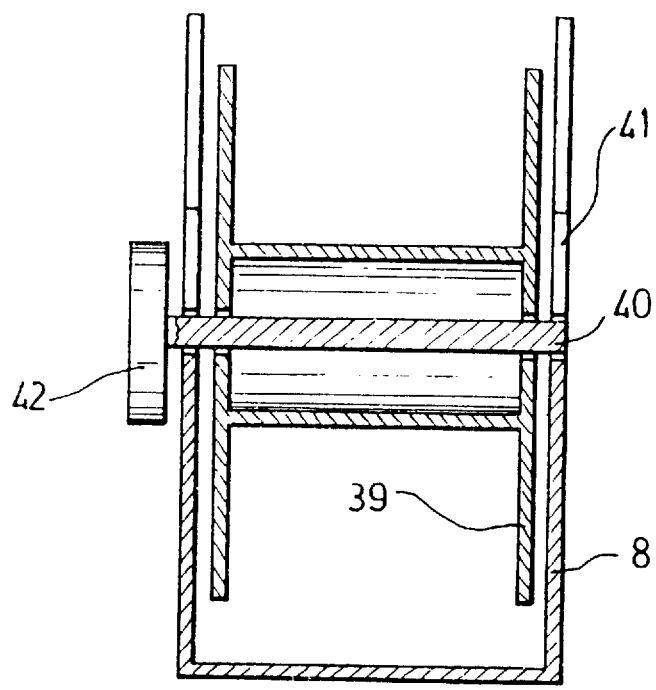
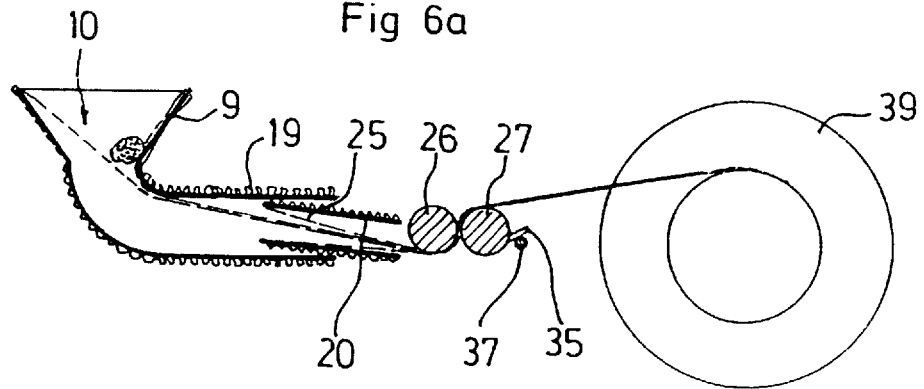

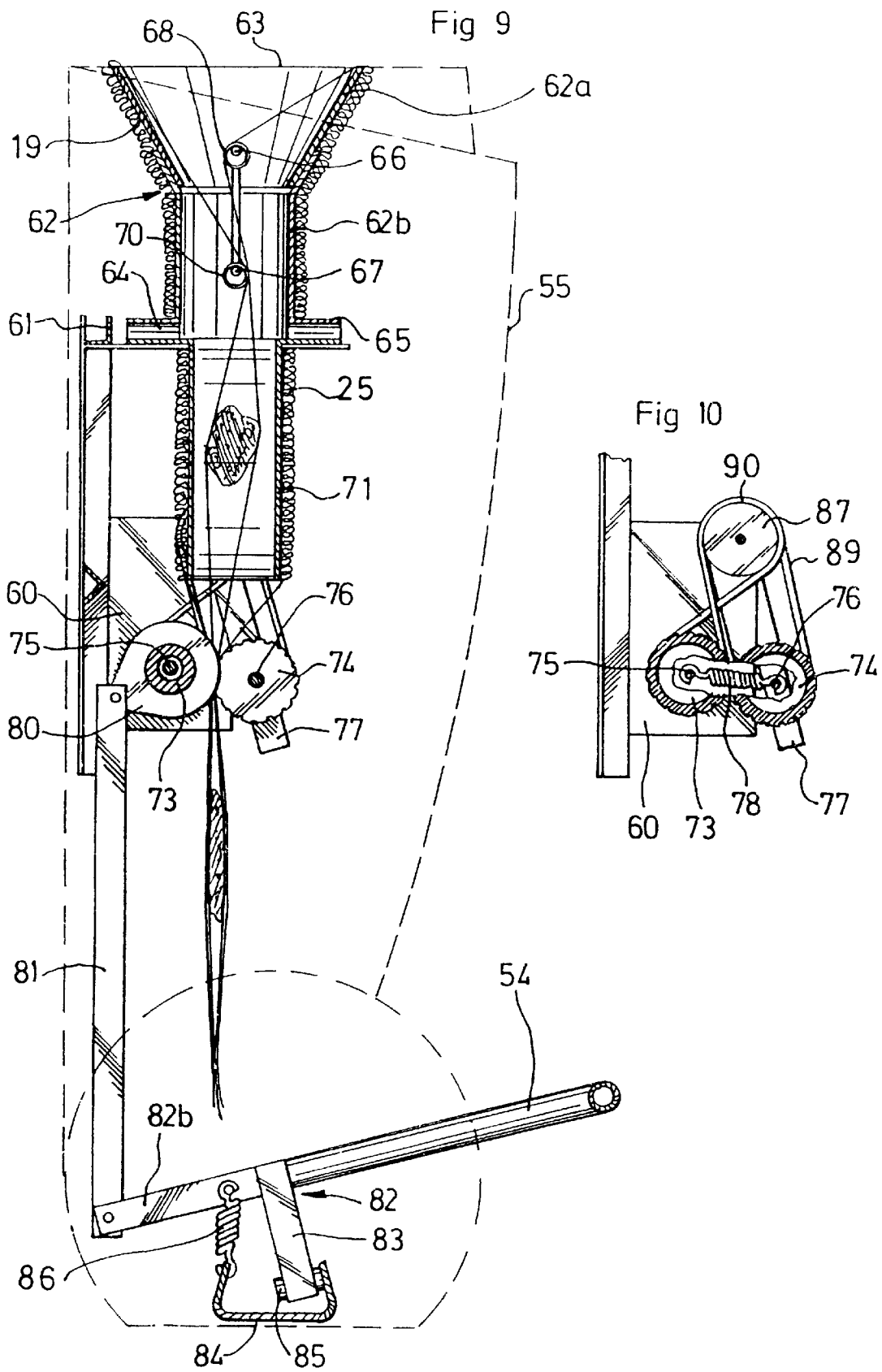

DEVICE FOR THE RECOVERY AND STORAGE OF WASTE

This invention relates to an apparatus for the recovery and storage of waste. In particular it relates to the recovery of hazardous waste such as hospital waste. Another application comprises the provision of a recovery and storage apparatus intended to be used as a water closet.

BACKGROUND AND OBJECTS OF THE INVENTION

The recovery and storage of waste, particularly hazardous waste, such as hospital waste, is carried out most often in an empirical manner using waste cans which, because of the need to be emptied and cleaned regularly, comprise a not-insignificant source of danger.

Further, and especially in the aeronautical field, the recovery and storage of waste which comprises human excrement poses serious problems of storage, giving rise at the present time to numerous research efforts seeking to solve these problems by means of drying by microwaves . . .

The present invention seeks to overcome these disadvantages and has as its principal object to provide an apparatus solving all of the above mentioned problems inherent in the recovery and storage of waste.

Another object of the invention is to provide an apparatus conceived to be able to operate in an autonomous manner.

Another object of the invention is to provide an apparatus permitting assurance of the treatment of waste, particularly in water closet applications.

DESCRIPTION OF THE INVENTION

To this end, the invention provides a waste recovery apparatus comprising:
- a receptacle provided with an opening for the introduction of waste,
- a sheath arranged around the receptacle on the exterior thereof, and invaginating into the interior of said receptacle through the opening, said sheath having a cross-section less than that of the receptacle and being able to expand radially,
- an obstacle for changing direction arranged downstream of the introduction opening, transverse with respect to the case, said obstacle being arranged to be positioned on the path of said sheath in such a manner as to incurve the path thereof,
- means for moving the sheath, adapted to cooperate with a portion thereof downstream of the direction changing obstacle, for:
    - maintaining constantly under tension the portion of the sheath situated upstream of said carrying away means in such a manner as to cause a closing of the sheath upon contact with the direction changing obstacle,
    - causing, on command, a displacement of the assembly of the sheath over a predetermined distance, in such a manner as to cause a new portion of the sheath to enter the receptacle,
- means for actuating the means for carrying away the sheath, and
- a zone for storage of the discarded sheath downstream of the carrying away means.

Because of its conception, such a device constitutes a "mechanical siphon" which permits "downstreaming" and immediately isolating waste discarded in the receptacle.

In effect, the sheath is constantly maintained under tension because of its radial elasticity and the conception of the carrying away means, is closed at right angles to the direction changing obstacle which constitutes the barrier beyond which the waste is isolated.

In addition, the portion of the sheath situated at the point of the opening of the receptacle and thus able to be placed in contact with a source of contamination, is renewed with each evacuation operation.

According to another characteristic of the invention, the receptacle has a tubular cross-section comprising an increasing cross-section, widening in the direction of the inlet opening.

This conical shape for the inlet of the receptacle permits assuring a complete radial unfolding of the sheath regardless of the manner that this sheath has been arranged around the receptacle.

Furthermore, according to a preferred embodiment, this apparatus advantageously comprises:
- a reel of tubular cross-section arranged between the direction changing obstacle and the sheath carrying away means, and arranged so that the sheath passes to the interior of the reel,
- a second sealed sheath stored around the reel on the exterior thereof and adapted to be unrolled around the first sheath, in such a manner as to encase the first sheath and to be drawn away therewith by the means for carrying away the sheath.

This encasing of the first sheath inside a sealed sheath represents a supplemental bacteriological barrier.

In addition, according to another characteristic of the invention, the apparatus comprises a pump adapted to be controlled by actuating means and provided with an aspiration inlet connected to a reservoir containing an antiseptic product, and having a discharge outlet connected to an injector arranged in the receptacle.

The vaporization of an antiseptic product comprises an active disinfection which assures a first bacteriological barrier and especially offers the possibility of assimilating hospital waste bagged according to the invention as managed waste.

According to a first preferred embodiment, the means for carrying away the sheath advantageously comprises:
- pulling means adapted to bring about a displacement of the sheath over a predetermined distance, in such a manner as to cause a new portion of the sheath to enter the receptacle,
- storage means situated in the storage zone and comprising an emptying spool carried by a rotating shaft, and means for rotatably driving said emptying spool for causing it to rotate an angular distance equivalent to the linear distance of displacement of the sheath, upon each actuation of the pulling means.

According to this embodiment, the device comprises storage means which permits maintaining the sheath under tension, and has the advantage of being manipulated easily and safely during changing and during transfer for ultimate treatment.

In this case, in other words, the pulling means comprises advantageously:
- two transverse rolls arranged in such a manner as to be located on opposite sides of the sheath, said rolls being secured, at the point of each of their ends, on an axis eccentric with respect to their longitudinal axis of symmetry,
- means for driving the rolls, controlled by actuating means and able to displace the assembly of said rolls along the sheath between an upstream position and a downstream position, return means able to return the rolls from their downstream position to their upstream position, means for pivoting the eccentric axes of the rolls and able to maintain said rolls:

in contact one with the other during their displacement from their upstream position toward their downstream position, so as to pull the sheath, pinched between the rolls, spaced from each other during their return from their downstream position to their upstream position.

Moreover, according to another characteristic of the invention, the pivoting means comprises, for each roll, a lever secured to the eccentric axis of the roll, and stop members upstream and downstream for causing rotation of said lever. Further, bistable elastic means are associated with the levers and arranged to maintain the rolls in one or the other of their relative positions, after pivoting of said levers.

Further, the means for rotatably driving the spool comprises advantageously a spring motor prestressed in a preliminary phase and adapted to cause a rotation of said spool when the rolls are in their spaced apart position.

An apparatus thus conceived has the advantage of being entirely autonomous by using, for example, for the actuating means, a member such as a pedal connected by a rod to the rolls.

According to a second preferred embodiment, the driving means comprises advantageously:

two transverse rolls each carried by a rotation shaft, arranged on opposite sides of the sheath so that the sheath may be held pinched between the rolls, means for rotatably driving the rolls, controlled by actuator means, able upon each command, to cause said rolls to rotate in a unidirectional manner without reversing, for a predetermined angular distance, means for shifting the rotation shaft of at least one of the rolls so as to permit the rolls to separate from each other, and return means connecting the rotation shafts of the rolls in such a manner as to exert a force tending to maintain the latter in contact with each other.

According to this embodiment, the tension of the sheath and holding it under tension are achieved by means of one assembly comprising as basic elements two rolls arranged to keep the sheath pinched.

Such driving means has the advantage of forming the equivalent of a rolling mill which grinds and compacts the waste, the passage of said wastes being made possible due to the ease of relative separation of the rolls.

Further, in order to improve the compacting without harming the sheath, the rolls advantageously comprise a peripheral face having grooves extending along the generatrices of the rolls.

According to a preferred embodiment concerning the drive means:

the rotational shaft of one of the rolls, called the fixed roll, is mounted so as to be fixed in translation, the rotational shaft of the other roll, called the movable roll, being secured to arms able to permit a rocking movement of the said movable roll with respect to the fixed roll, the rotational drive means of the rolls comprises unidirectional drive means for the fixed roll, associated with actuating means, and transmission members able to transmit this rotational movement, in a reverse manner, to the movable roll.

Such transmission members advantageously comprise, in addition:

a double groove pulley mounted coaxially with respect to the axis of rotation of the arms, two pulleys, one secured to the rotational shaft of one of the rolls, two belts connecting each pulley of one of the rolls to the double groove pulley and arranged in such a manner as to invert the direction of rotation of the movable roll with respect to that of the fixed roll.

Further, two preferred embodiments are provided according to the invention, concerning the obstruction for changing the direction.

According to a first variation of this embodiment this obstruction for changing direction comprises an elbow arranged in the extension of the opening and arranged such that the sheath recloses itself upon contact with that upper portion called the elbow.

This first embodiment is particularly adapted but not specifically restricted to the production of an apparatus in which the different elements are arranged one after another.

In this case, these elements, in particular the receptacle, the pulling means and the storage means are preferably housed on the interior of a cabinet, the receptacle and the storage means moreover being mounted in a removable manner in said cabinet.

In order to have this removable character, the receptacle comprises, preferably, two transverse axles, fixed externally on and beneath said receptacle near an end opposite to the introduction opening. In a parallel manner, the cabinet has four slides arranged to slidingly receive the axles of the receptacle, and provided at their ends with members for blocking said axles from translational movement.

Further, the reel is preferably adapted to come to be housed over its greatest length in the receptacle, downstream of the elbow, and comprises two transverse axles fixed externally on and above said reel, toward one of the ends thereof, said axles, of a length less than the axles of the receptacle being carried at the level of each of their ends by a removable piece connecting with one axle of the receptacle. It should be noted that the sealed sheath is then stored around the reel in such a manner as to invaginate itself on the interior of the latter.

Moreover, in view of the removability of the spool, the housing advantageously comprises two grooves inclined with respect to the vertical, able to house the ends of the rotational shaft of the spool.

According to another characteristic of the invention, the apparatus comprises a cart able to support the housing, and provided with a covering comprising a removable cowling pierced by an opening conjugate with the introduction opening for the receptacle.

Moreover, in the case in which one desires a very great asepsis, this apparatus may also integrate in an advantageous manner, aspiration means able to create a depression of pressure on the interior of the cowling, and means for filtering the air returned by the aspiration means.

According to the second variation of this embodiment concerning the obstacle for changing direction, this latter is comprises two parallel axles, called upstream and downstream, arranged transversely at a distance one from the other in such a manner that during passage of the sheath between said axles, the trajectory of the latter is recurved in such a manner that said sheath recloses upon contact with the downstream axle.

This second embodiment is particularly adapted, but not specifically restricted, to the fabrication of an apparatus in which the receptacle, the driving means for the sheath, and the storage zone are arranged one beneath the other.

Such an apparatus comprises, in addition, advantageously, a shell provided with an upper opening, able to house the receptacle and the driving means, and defining in its lower portion an accessible storage zone, the receptacle being mounted in a removable manner in said shell.

Moreover, in order to permit an easy changing of the two sheaths and in a preferred manner:

the sealed sheath is stored around the reel in such a manner as to empty itself in the lower extension of the reel, around the first sheath leaving the latter, the reel presents a upper collar arranged to permit suspending the reel on the interior of the housing provided for that purpose with support elements for said collar, the receptacle is arranged to come to rest on the collar of the reel.

According to another characteristic of the invention, the receptacle has an oval, tubular cross-section and comprises an upper portion of an increasing cross-section widening in the direction of the introduction opening, and a lower portion of a constant cross-section. Further, the axles extend along the greater dimension of the receptacle, the upstream axle being arranged in the upper portion of said receptacle, and the downstream axle being arranged in the lower portion and being connected to the upstream axle in such a manner as to be able to flip-flop relatively to the latter.

This flip-flopping or rocking of the downstream axle has the advantage of increasing the size of the waste able to be absorbed.

The apparatus according to the invention is also conceived to be able to serve as a water closet. In this case, in an advantageous manner:

the receptacle is shaped, downstream of the elbow, in such a manner as to constitute a recovery tank for liquids, provided with an evacuation outlet for said liquids, the first sheath has a texture adapted to allow flow of liquids through the sheath toward the recovery tank, treating means are adapted to assure the treatment of the recovered liquid with a view toward permitting its discharge or use.

Such an apparatus permits, in the first place, a solution to the obstructive problems which water closets have in the aeronautical field. Moreover, it assures a separation of excrement which permits a storage of the solid matter, (feces, paper . . . ) and treating the liquids in such a manner as to permit, after final treatment, either discarding of the latter or its reuse, for example for washing hands. It should be noted, to this end, that the recovery of the impurities found in the liquids is done in a manner preponderantly within the tank of the receptacle which is removable and therefor very easily cleaned.

Further, the opening or the receptacle is recurved with a portion of the sheath which is automatically renewed between each use.

According to one preferred embodiment, the treatment means comprises means for the centrifugation of liquids, means for the pressurization of recovered liquids, and means for filtration to which the liquids are delivered under pressure.

Further, this apparatus is preferably housed in an enclosure comprising aspiration means able to create a reduced pressure on the interior of the enclosure, and means for filtration of air withdrawn by the aspiration means.

Other than the reduced encumbrance, this enclosure and the material enclosed has a weight notably reduced with respect to existing installations, which translates to a great advantage with respect to the latter in one field, aircraft, where any weight savings is greatly appreciated.

BRIEF DESCRIPTION OF THE DRAWINGS

Other characteristics, objects and advantages of the invention will become apparent from the detailed description which follows in reference to the accompanying drawings which show, by way of non-limiting example, three preferred embodiments. In these drawings which form an integral part of the present description:

FIG. 5 is a transverse cross-sectional view along a vertical plane B of FIG. 3 of this first variation of the apparatus according to the invention;

FIGS. 6a to 6d are schematic view illustrating the operation of this device;

FIG. 9 is a longitudinal cross-section along a transverse plane C of the module shown in FIG. 8;

FIG. 10 is partial longitudinal cross-section along a transverse plane D of the module shown in FIG. 8, FIGS. 11 to 11c are schematic views showing the operation of this module.

DESCRIPTION OF PREFERRED EMBODIMENTS

The devices shown in FIGS. 1 to 5 and 7 to 10 comprise respectively a cart and a vertical module intended for the recovery, treatment and storage of waste material, especially in the medical field. These devices are conceived for functioning in an autonomous manner without the need for a contribution of energy.

Figure 12:
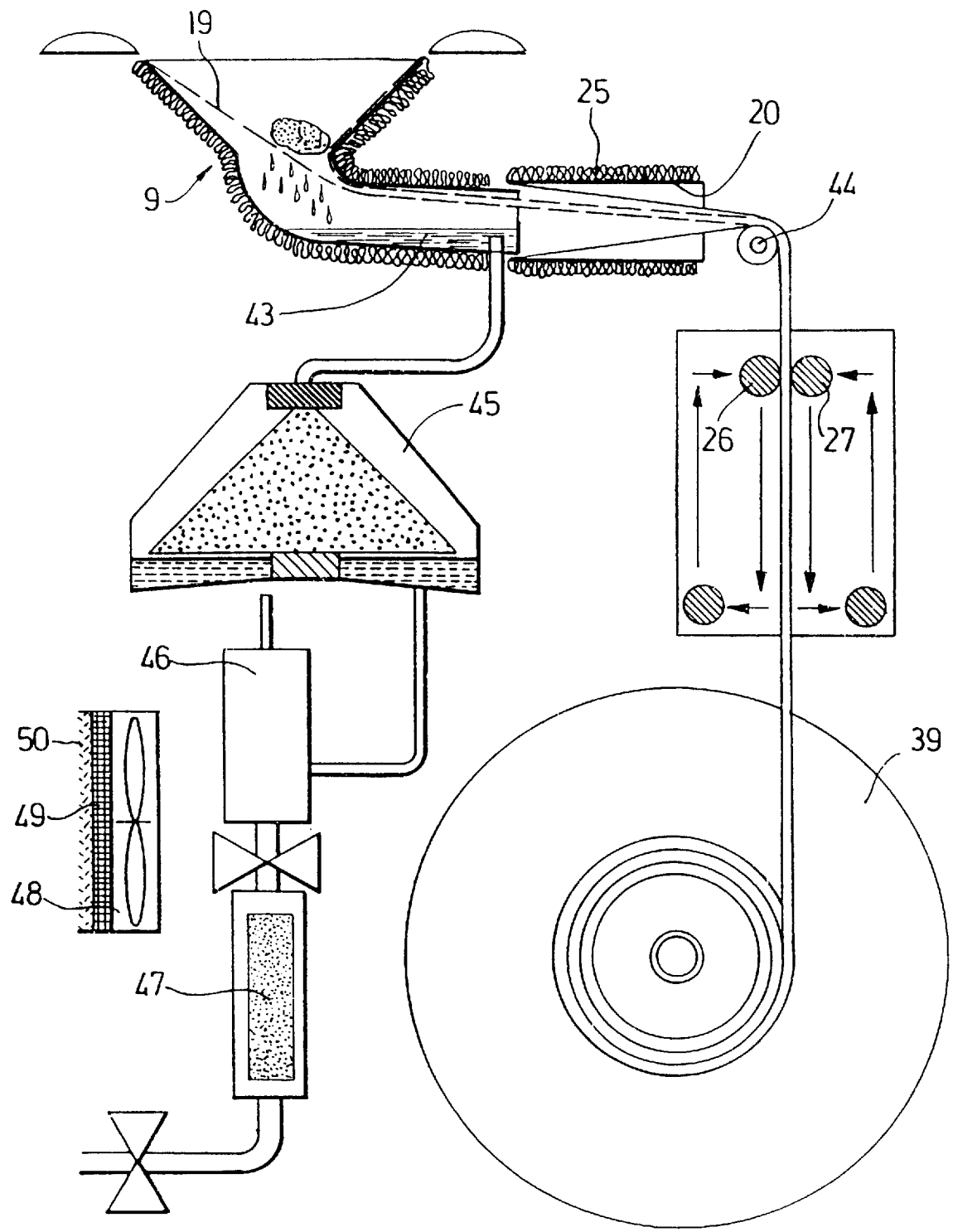
FIG. 12 is a functional schematic of an apparatus according to the invention used as a water closet.

The device shown in FIG. 12 constitutes a water closet particularly intended to be used in the aeronautical field.

Figure 1:
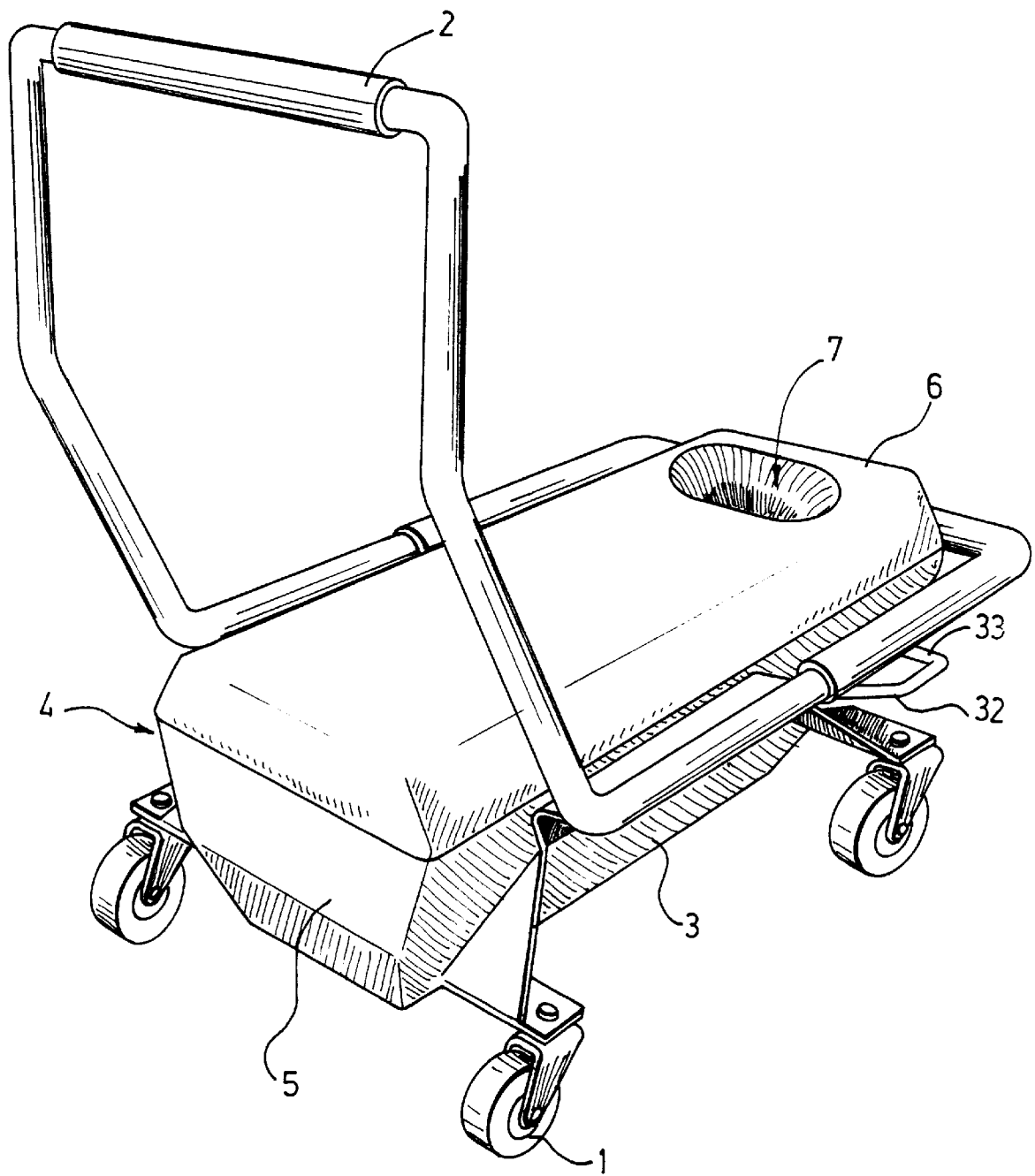
FIG. 1 is a perspective view of a cart equipped with a first variation of the apparatus according to the invention.

The device shown in FIG. 1 comprises a cart mounted on wheels 1 and provided with a handlebar 2. This cart includes a chassis 3 carrying a body 4 composed of a fixed shell 5 on the chassis 3 and a removable cowling 6. This cowling 6 is, in addition, pierced by an opening 7 of an ovoid shape comprising the inlet opening for the introduction of waste materials.

Figure 2:
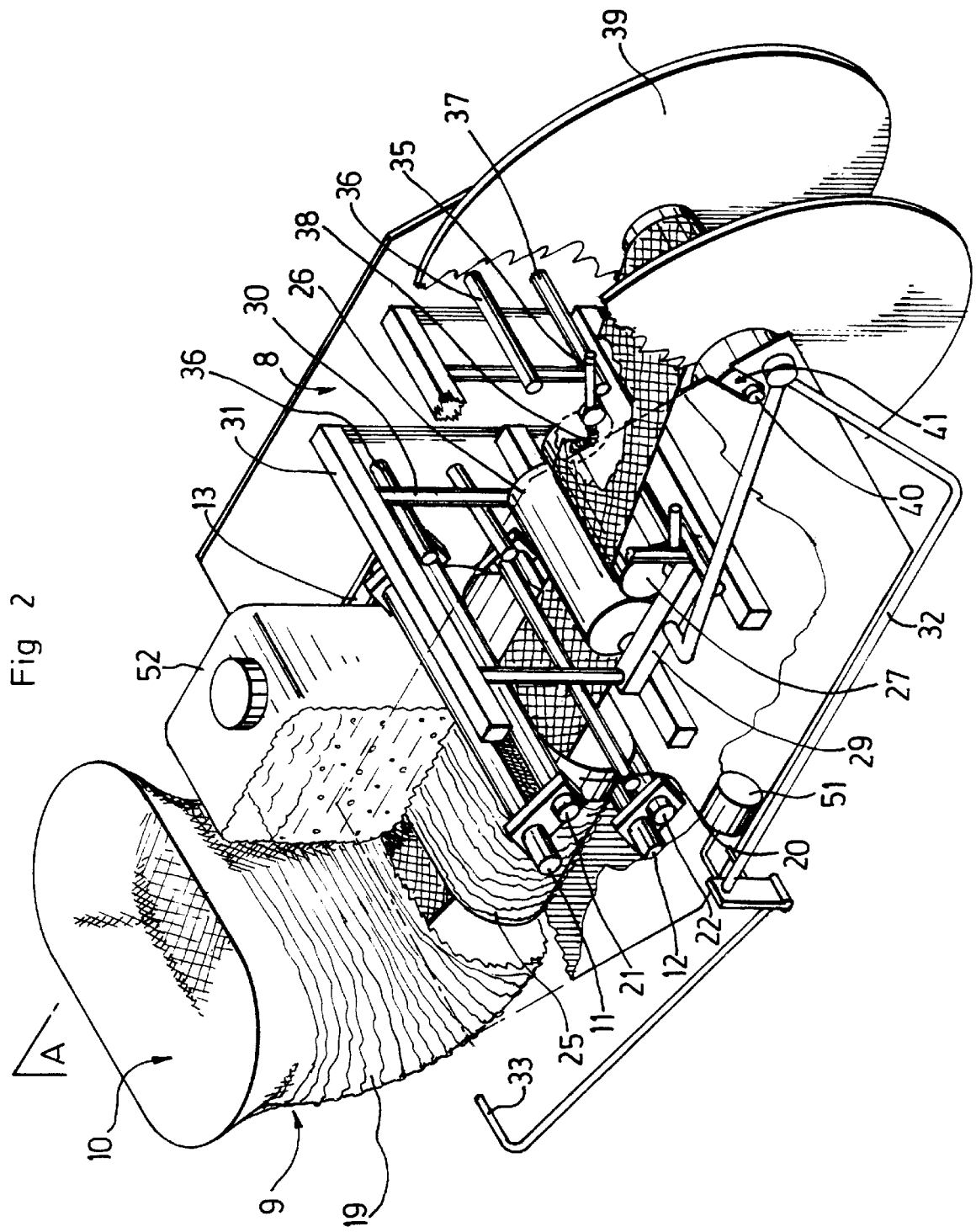
FIG. 2 is a perspective view with portions broken away, of this first variation of the apparatus according to the invention.
Figure 3:
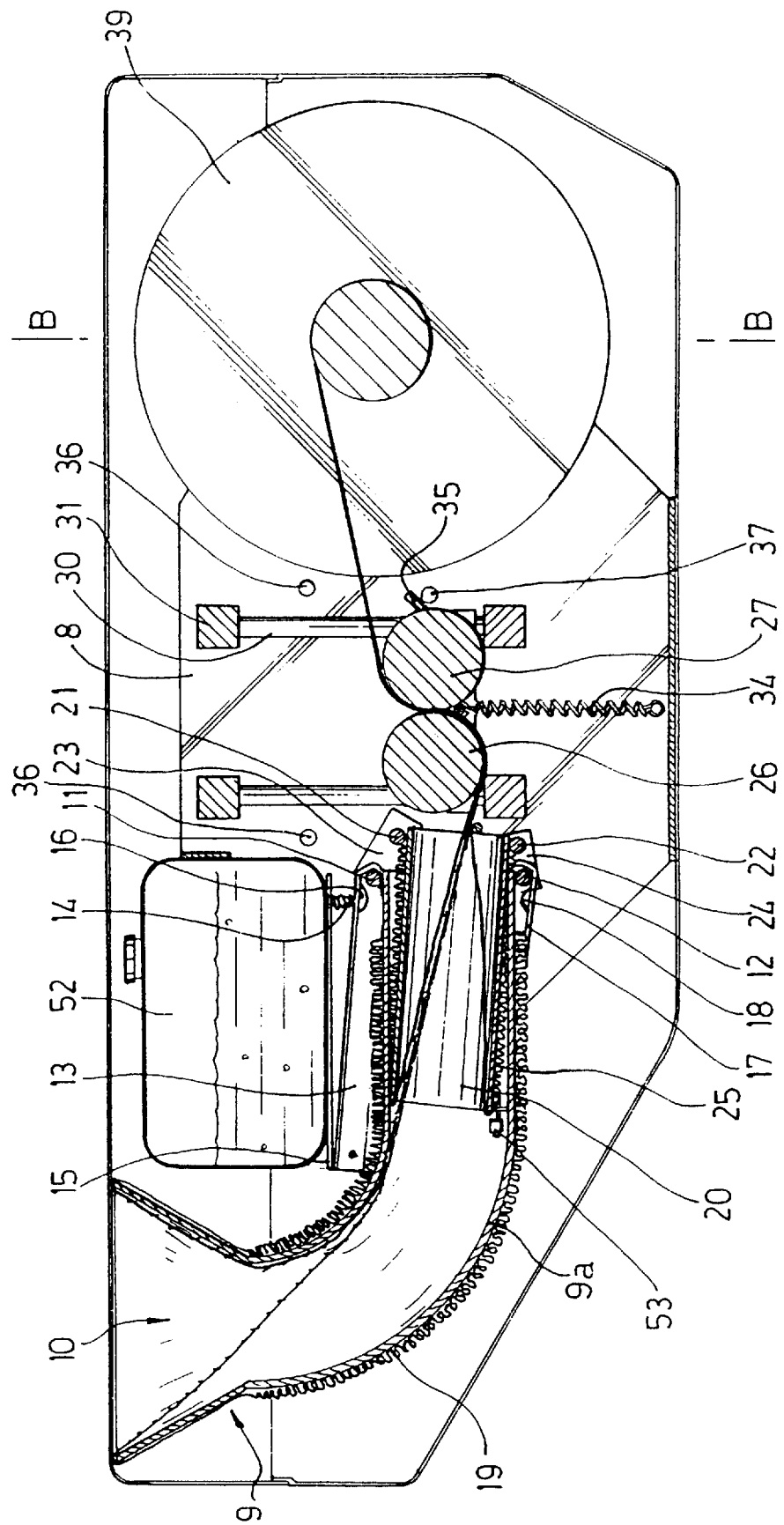
FIG. 3 is a longitudinal cross-sectional view along vertical plane A of FIG. 2.
Figure 4:
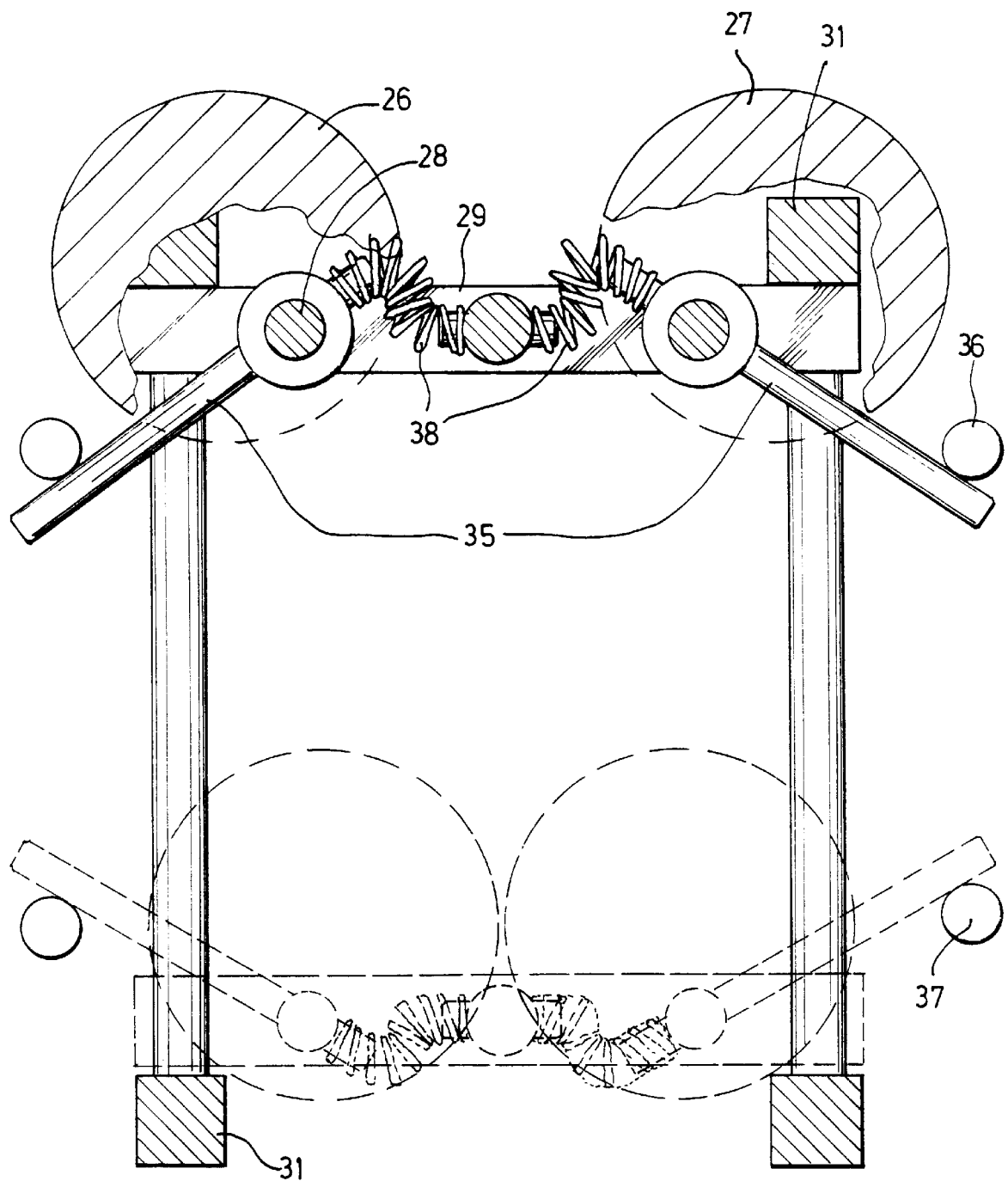
FIG. 4 is a cross-sectional view on an enlarged scale, of the pulling means for this apparatus, illustrating the two positions, upstream (in dotted lines) and downstream (in solid lines) of the pulling means.

The waste recovery device is, itself, integrated within the interior of the body, and as shown in FIGS. 2 and 5, housed on the interior of a casing 8 comprised of a sheet metal having transversely a generally U-shaped form.

This device comprises, in the first place, a removable receptacle 9 made up of a tubular element of stainless steel of an oval cross-section with its major axis horizontal, having longitudinally an elbow shape.

This receptacle 9 is provided with an opening 10 for the introduction of waste materials and is positioned in such a manner that the opening 10 is opposite the opening 7 of the cowling 6. It also has between the elbow 9a and this opening 10, an increasing cross-section, conferring upon it a funnel shape.

The receptacle 9 comprises in addition two transverse axles 11, 12 fixed externally on and over said receptacle, at the point of its end opposite the opening 10.

In order to support this receptacle, the device comprises four L-shaped slides secured in opposing pairs on the internal faces of each of the sides of the casing 8, and each being intended to house one end of a transverse axle 11, 12.

These slides comprise, in the first place, two upper slides 13 articulated on the sides of the casing 8, at their end provided for introduction of the axle. Each of these upper slides 13 is in addition kept inclined with respect to the horizontal at a slope declining in the direction of introduction of the axles 11, by means of a spring 14, interposed between the end of said slide opposite the axis of articulation and a horizontal platform 15 arranged above the latter.

Each slide 13 comprises further a member 16 for blocking the axle 11 in translation, arranged in such a manner as to protrude to the interior of the slide, in proximity to its end opposite to the axis of articulation.

The slides comprise in the second place two lower fixed slides 17 equally arranged along a declining slope, and intended to house the lower axles 12 of the receptacle 9. In the same manner as the upper slides 13, the lower slides 17 comprise a blocking member 18 for the axles 12.

The device further includes a sheath 19 of a radially expandable textile material, compressed radially in its normal position. This sheath which comprises a consumable element has a length of several meters, and is intended to be disposed in an accordion fashion around the receptacle 9, and to be invaginated on the interior of the latter through the opening 10.

It will be noted that due to the "funnel shape" of the receptacle, the sheath 19 is perfectly stretched and smooth to the right of the opening 10.

The apparatus comprises further a reel 20 comprising a rectilinear tubular element of an oval cross-section with dimensions less than those of the receptacle 9, adapted to be housed over its greatest length on the interior of this receptacle 9.

This reel 20 comprises at one of its extremities, two transverse axles 21, 22 of a length less than those of the axles 11, 12, fixed externally above and below the reel.

It is connected to the receptacle 9 by means of two connecting pieces, an upper 23 and a lower 24, each inserted into orifices arranged to house respectively one of the axles 11, 12 of the receptacle 9, and one of the axles 21, 22 of the reel 20.

The apparatus comprises further a second sheath 25 of a plastic material constituting a second consumable element. This sheath 25 is intended to be disposed in an accordion fashion around the reel 20 and to be invaginated inside of the latter in such a manner as to encase the textile sheath 19.

The device also comprise pulling means adapted to cause, upon command, a simultaneous displacement of about ten centimeters of the two sheaths 19, 25.

This pulling means comprises, in the first place, two transverse rolls 26, 27 arranged horizontally and between which the sheaths 19, 25 are caused to pass. These two rolls 26, 27 are provided at each of their ends, with an axle 28 eccentric with respect to their longitudinal symmetry.

These rolls 26, 27 are further mounted between two horizontal bars, such as 29, provided with blind holes arranged to house their axles 28 while permitting rotating of said axles. These two bars 29 are, themselves, mounted slidingly along vertical columns such as 30 extending between the two sides of the casing 8.

The pulling means comprises, in addition, means for translationally driving the rolls 26, 27 for generating a sliding toward the top of the bars 29 along the columns 30.

This driving means includes a linkage system 32 comprised of two elements arranged on opposite sides of the casing 8 and articulated on the sides thereof, said elements being connected toward one of their ends by a transverse rod 33 forming a pedal accessible from in front of the cart, and being secured toward its other end to one of the bars 29.

The pulling means also comprises return means able to generate a sliding movement toward the bottom of the bars 29 along the columns 30, while the pressure on the pedal 33 is relaxed. This return means comprises springs 34 arranged vertically and secured to the casing 8 and to one bar 29.

The pulling means finally comprises means for pivoting the rolls 26, 27 in order to support the latter:

in contact with each other during their upward displacement, generated by an action on the pedal 33, such that it pulls the sheaths 19, 25 pinched between them, spaced apart from each other during their return to their lower position, generated by the springs 34.

This pivot means comprises, in the first place, levers 35 secured to the axles 28 of each roll 26, 27, and extending orthogonally with respect to the latter.

The pivoting means comprises, in addition, for each roll 26, 27, two portions of transverse bars 36, 37 fixed orthogonally on the sides of the casing 8, respectively the upper and lower stops, able to cause the rotation of the levers when the rolls 26, 27 arrive at their upper and lower positions.

The pivoting means finally comprises bistable springs 38 connecting the levers 35 to the bars 29, and adapted to maintain said levers in the positions corresponding to the contacting or spaced positions of the rolls 26, 27 after rotation thereof.

The invention furthermore includes, downstream of the rolls 26, 27, an interchangeable spool 39 for storing the sheaths 19, 25. This spool 39 is provided with a rotation axle 40 extending beyond the end flanges of the spool and coming to be housed in the grooves 41 inclined with respect to the vertical axis provided in each of the sides of the casing.

This spool 39 is further associated with a spring motor 42 secured on its rotational axle 40. This spring motor 42 prestressed in a preliminary stage, is adapted to rotatably drive the spool 39 when the rolls 26, 27 are spaced apart from each other, and thus bring about the taking up of the length of the sheaths 19, 25 pulled by these rolls.

Finally, the drum of the spool 39 is covered with a hooking device such as a band of "Velcro," permitting attaching the end of the sheaths 19, 25 after a replacement of the spool.

In the last place, the apparatus comprises active disinfecting means comprising a mechanical pump 51 arranged to be actuated by the linkage 32 when the pedal is maneuvered.

This pump 51 is connected on its aspiration side to a reservoir 52 containing an antiseptic product, arranged on the platform 15, and on its pressure side to an injector 53 arranged in the receptacle 9, which permits impregnating the portion of the sheath 19 encircling the waste introduced therein with the antiseptic product in the receptacle.

The operation of the apparatus described hereinabove is illustrated in FIGS. 6a through 6d.

In the rest position shown in FIG. 6a, the rolls 26, 27 are in their lower position and are in contact with each other, holding the sheaths 19, 25 pinched along a transverse line.

Figure 6B:
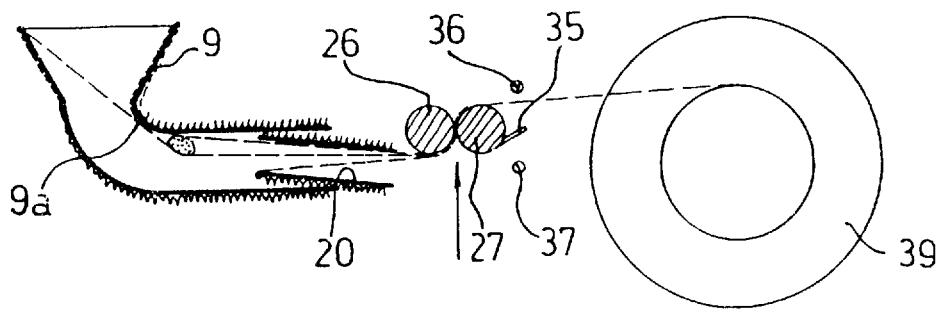

After introduction of waste material, an activation of the pedal 33 causes an upward displacement of the rolls 26, 27, still held together, and thus brings about a displacement of the sheaths 19, 25 (FIG. 6b). This displacement causes the "downstreaming" of the waste which is brought downstream of the elbow 9a of the receptacle 9 and is thus isolated from the external environment.

Figure 6C:
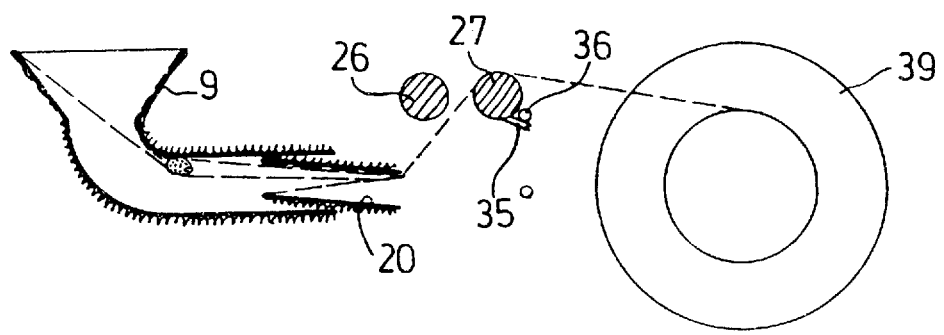

Further, when the rolls 26, 27 arrive at the end of their travel, the levers 35 arrive at their upper stop against the transverse bars 36 and 37, causing a rotation of said rolls and bringing about their relative separation (FIG. 6c).

Figure 6D:
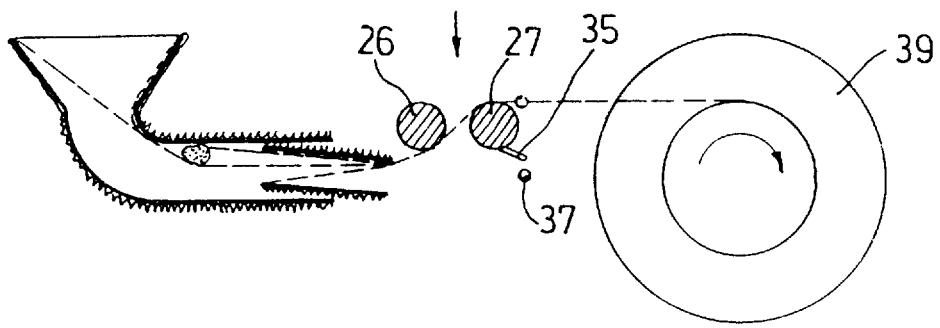

Thus, when the pedal 33 is relaxed and the rolls 26, 27 fall under the action of the springs 34, the spool 39 may absorb, under the action of the spring motor 42, the length of the sheaths 19, 25 initially withdrawn (FIG. 6d).

The waste thus moved downstream is impregnated with the antiseptic product either immediately or upon a subsequent pedal actuation for a subsequent waste recovery step. Moreover, during the subsequent actuations of the pedal 33, the portion of the sheath 19 surrounding this waste is encased on the interior of the plastic sheath 25.

Figure 7:
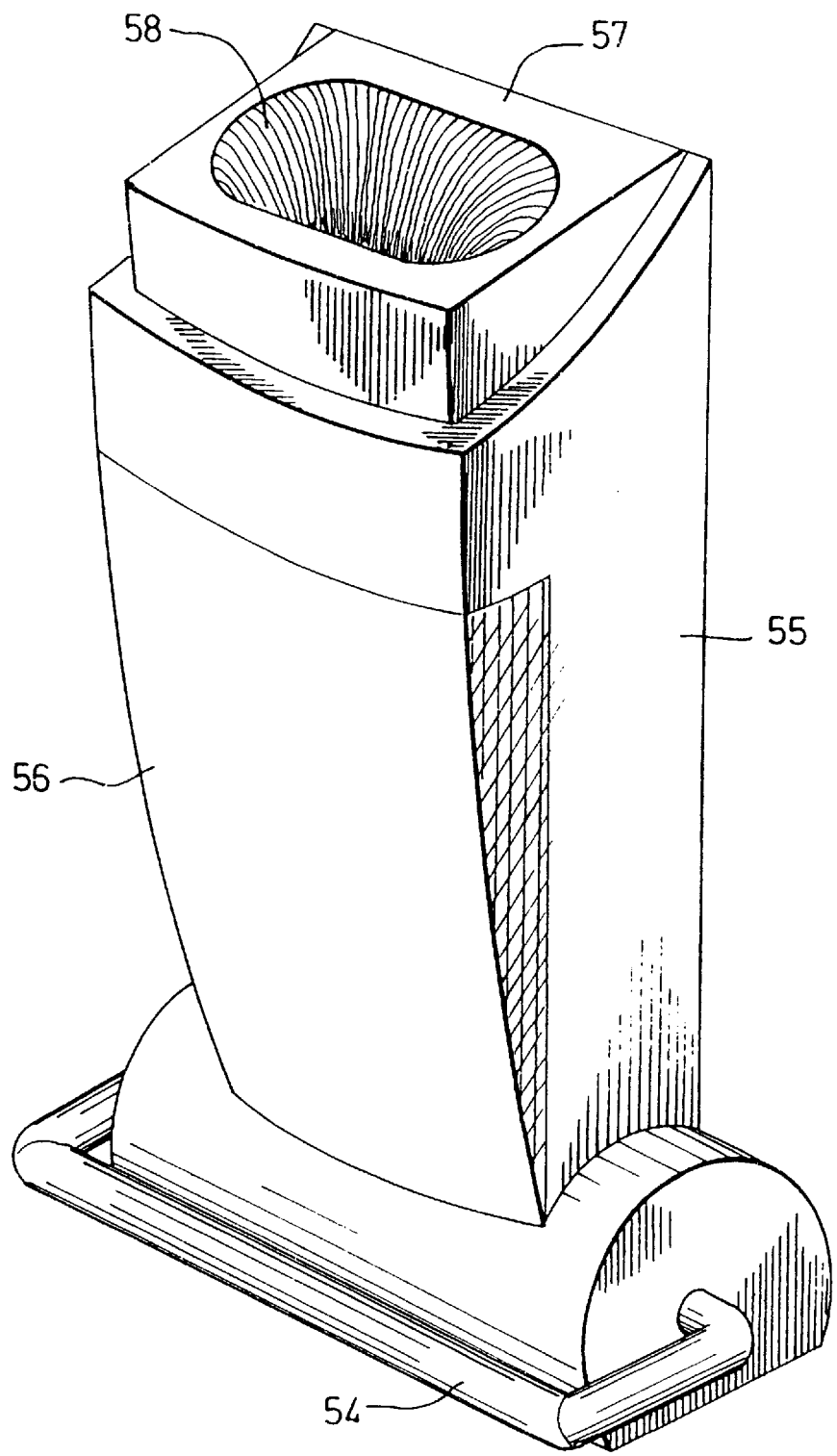
FIG. 7 is a perspective view of a vertical module equipped with a second variation of the apparatus according to the invention.

The apparatus shown in FIG. 7 comprises a vertical module provided with a handlebar 54 in the lower part. This module is comprised of a self-supporting shell 55 provided with a front wall 56 and a one-piece cover 57 pivotally mounted about a vertical axis. The cover 57 is pierced by an opening 58 of an oval shape comprising the opening for introduction of the waste material.

Figure 8:
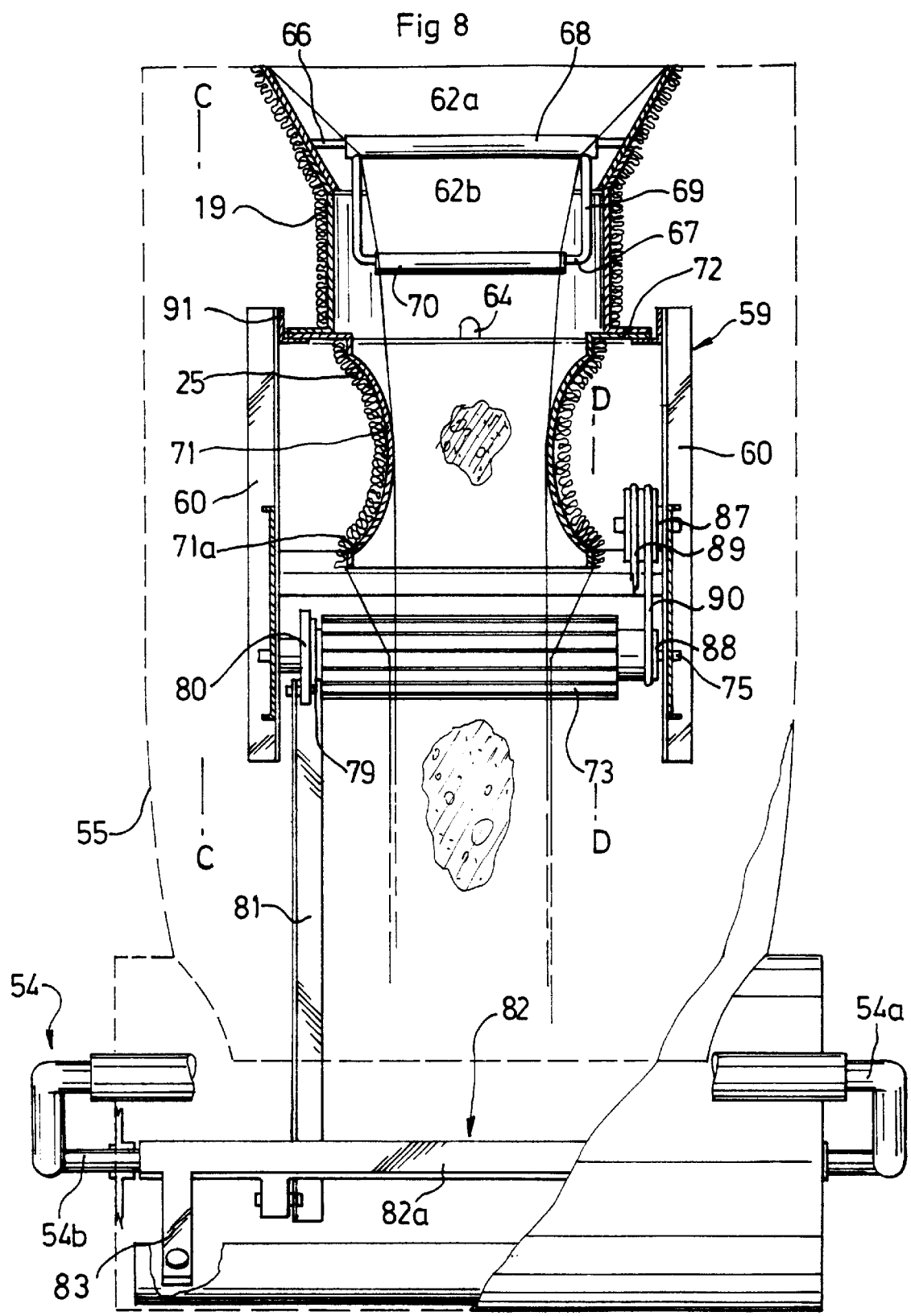
FIG. 8 is a front view partially in cross-section, along a transverse vertical plane of the module of FIG. 7.

The waste recovery apparatus itself is integrated on the interior of the shell 55 and, as shown in FIGS. 8 to 10, mounted on a chassis 59 comprising primarily two lateral flanges such as 60 connected by transverse front pieces such as 61.

This recovery device comprises, in the first place, a removable receptacle 62 constituted by two tubular elements of oval cross-section and made of resinous material, intended to interfit one into the other. This receptacle 62 comprises thus an upper portion 62a expanding upwardly, terminating by a waste introduction opening 63 of a shape conjugate with the opening 58 in the shell 55.

This receptacle 62 comprises also a lower portion 62b of a constant oval cross-sectional shape in which the upper portion 62b comes to fit. It comprises finally two orifices such as 64 arranged opposite each other in the lower part respectively of the front and rear walls of the lower portion 62b, said orifices being extended externally by two horizontal sleeves such as 65.

As previously, this receptacle 62 is covered by a sheath 19 arranged in an accordion fashion around the latter, and intended to invaginate on the interior thereof through the opening 63. This sheath 19 is arranged only around the lower portion 62b which therefor constitutes, with this sheath, a consumable element, the upper portion 62a not having to be interchanged.

The receptacle 62 integrates two transverse axles, called upstream 66 and downstream 67 arranged horizontally on the interior of said receptacle, and extending according to the greater dimension and in one of the planes of symmetry of the latter.

The upstream axle 66 extends in the upper portion 62a of the receptacle 62 and is secured at the lever of each of its ends, to the wall of said receptacle, for example by immersing said ends in the resin.

This upstream axle 66 is, furthermore, housed over a great portion of its length, on the interior of a tube 68 freely rotatable and freely translatable with respect to the axle.

The downstream axle 67 extends itself, into the lower portion 62b of the receptacle 62, and forms the core of a U of which the upper ends of the sides 69 are soldered on the tube 68. Thus arranged, this downstream axle 67 is suspended from the tube 68 and may flip-flop from side to side of the plane of symmetry of the receptacle 62 and thus permits the passage of waste material of a size greater than that which would be permitted by a fixed axle.

Moreover, this downstream axle 67 is housed over its greatest length on the interior of a tube 70 intended to reduce the frictional forces between the sheath 19 and said axle.

The apparatus comprises further a reel 71 intended to be disposed in the lower extension of the receptacle 62, and serves to support the latter.

To this effect, the reel 71 has an upper face of dimensions essentially lower than those of the lower portion 62b of the receptacle, said face being provided with an external flange 72 arranged to carry said receptacle.

The reel itself is suspended between the two flanges 60 and rests through the intermediary of its external flange 72 on the horizontal flange of the corners 91, the vertical flange of which is secured to said flanges 60.

The reel 71 has further a rectangular tubular cross-section, and comprises two lateral walls 71a presenting longitudinally a concave shape.

As before, this reel 71 is covered with a sealed sheath 25 of a plastic material intended to be unwound into the lower extension of said reel, in such a manner as to encase the first sheath 19. It should be noted that to this end, the concave shape of the lateral faces 71a of the reel permits storing a greater length of the sheath 25 about the reel.

The apparatus also comprises driving means able to generate on command a simultaneous displacement of about ten centimeters of the two sheaths 19, 25.

This driving means comprises, in the first place, two transverse rolls 73, 74 closely together longitudinally, each mounted on a rotation shaft 75, 76, and arranged horizontally in such a manner that the sheaths 19, 25 are caused to pass between them.

These two rolls 73, 74 intended to hold the sheaths by pinching, present in addition peripheral faces provided with grooves extending along their generatrices, able to intermesh with one another.

Further, the rotation shaft 75 of one of these rolls 73, called the fixed roll, extends between the flanges 60 to which it is secured in translation.

By contrast, the rotational shaft 76 of the other roll, termed the movable roll, extends between two levers 77 articulated on the flanges 60 in such a manner as to be able to pivot about a horizontal axis and thus permit the movable roll 74 to swing relatively to the fixed roll 73.

Moreover, the axles of rotation 75, 76 of the two rolls 73, 74 are connected by a spring 78 tending to oppose swinging of the movable roll 74, and tending as a consequence to hold the two rolls in contact with each other.

The driving means for the sheaths 19, 25 comprises also means for rotationally driving the rolls 73, 74, able to cause them to rotate in opposite directions in a one directional manner by the actuation of the handle bar 54.

This rotational driving means is associated with the fixed roll 73, transmission members being disposed between said fixed roll and the movable roll 74 in order to transmit, while reversing, the rotational movement.

The means for driving in rotation comprises, in the first place, a unidirectional transmission member such as a free wheel system schematically illustrated at 79, secured to one of the ends of the rotation shaft 75 of the fixed roll 73.

It comprises in addition a return cam 80 arranged to cooperate with the transmission member 79, said return cam being secured to the upper end of a vertical connecting rod 81 adapted to cause the rotation of this cam at the time of its longitudinal displacement.

The rotational driving means comprises finally an actuating system connecting the handlebar 54 to the lower end of the connecting rod 81. It should be noted that to this end, the handlebar 54 has the shape of a U of which the sides are extended in return orthogonally to the sides, the center of said U forming a transverse actuator 54a, arranged upstream of the shell 55, and the returns forming two aligned pivot axes 54b extending through openings provided in the lateral walls of said shell.

The actuation system comprises a lever 82 provided with a crosspiece 82a extending between the returns 54b of the handlebar 54 and secured thereto, and a branch 82b orthogonal to the crosspiece 82a and articulated, towards its end, to the connecting rod 81.

This lever 82 comprises in addition a stop piece 83, orthogonal to the crosspiece 82b and to the arm 82b, arranged to limit the displacement of said lever, in association with a stop socket 84.

To this end, the stop socket 84 has a cross-section having the shape of a U of which the sides are essentially inclined toward each other, and the end of the foot 83 of the lever 82 is housed on the interior of said socket, in such a manner as to see its travel limited by the sides of this latter. The end of this shoe 83 is, in addition, provided with rubber bumpers 85 arranged so as to be interposed between the stop and the sides of the socket.

The actuating system comprises, finally, a spring 86 arranged between the arm 82b of the lever and one of the sides of the socket 84, and adapted to bring the connecting rod toward its lower position once the pressure on the handlebar 54 is relaxed.

The transmission members arranged between the fixed roll 73 and the movable roll 74 comprise, in the first place, a double groove pulley 87 secured to one flange 60 and coaxial with the pivot axis of one of the levers 77.

These transmission members comprise further two pulleys such as 88, each secured to a roll 73, 74. They comprise further two drive belts 89, 90 respectively direct (mounted normally) and reversing (mounted in a figure eight) each connecting the double groove pulley 87 to the pulleys 88.

This apparatus is also provided with a pump and a reservoir (not shown) similar to those of the device comprising the first embodiment, the pump being arranged to be actuated when the handlebar 54 is depressed, and the injectors being housed in the sleeves 65 of the receptacle.

The operation of the apparatus described above is shown in FIGS. 11a to 11c.

Figure 11A:
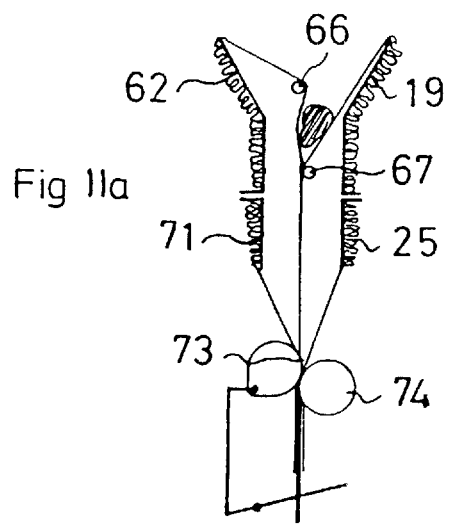

In the rest position shown in FIG. 11a, the sheath 19 is held under tension between the opening 63 of the receptacle and the rolls 73, 74, and is closed upon contact with the downstream axle 67.

Figure 11B:
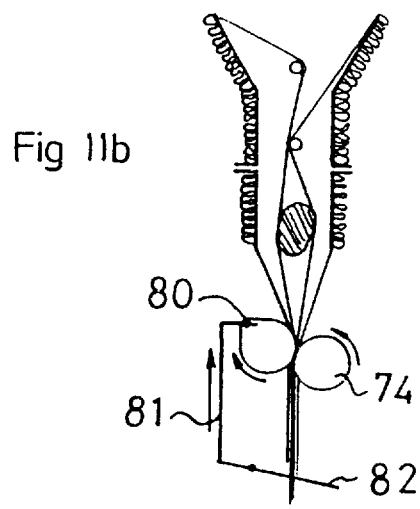

After the introduction of waste material, an actuation of the handlebar 54 causes a pivoting of the lever 82 which generates an upward displacement of the connecting rod 81, and consequently a rotation of the return cam 80 transmitted by the unidirectional transmission member 79 to the fixed roll 73 (FIG. 11b).

This rotational movement is then transmitted in a reverse direction to the movable roll 74 through the intermediary of the system of pulleys 87,88, belts 89, 90.

This rotation of the rolls 73, 74 causes a linear displacement of the sheaths 19, 25 held pinched between the said rolls, and as a consequence the waste is carried downstream of the downstream axle 67, and isolated from the external environment by virtue of the fact that the sheath 19 constantly held under tension, is reclosed by the downstream axle.

Once the pressure on the handlebar 54 is relaxed, the lever 82 is caused to pivot under the action of the spring 86, generating a downward displacement of the connecting rod 81 and as a result a rotation of the return cam 80. By contrast, the transmission member 79 being unidirectional, the roll 73 is not subject to any rotation and the tension of the sheath 19 is maintained.

Figure 11C:
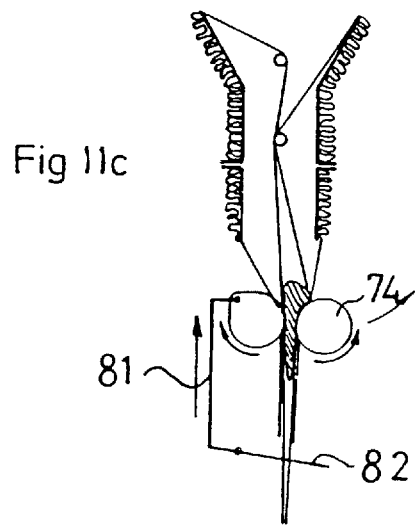

Further, as shown in FIG. 11c, when the waste arrives between the two rolls 73, 74, the movable roll 74 is caused to swing in such a manner as to allow a space sufficient to permit the passage of said waste. However, this swinging is limited by the action of the spring 78 which tends to return the rolls 73, 74 together, and which causes crushing of the waste between the rolls, much like a crushing mill.

The apparatus shown schematically in FIG. 12 is of the same conception as that described with reference to FIGS. 1 to 5 but enables a different application, in particular the provision of a water closet adapted for aeronautical use.

In this application, the receptacle 9 serves as the bowl of the water closet and is shaped so as to constitute a tank 43 for the recovery of liquids which flow through the sheath 19.

The reel 20 is itself arranged downstream of the receptacle 9, and a discharge wheel 44 is arranged downstream of the reel permitting a limitation of the space needed for the length of the water closet.

The pulling means and the spool 39 are identical to those described in reference to FIGS. 1 to 5, the only difference resulting from the reversal of the direction of displacement of the rolls 26, 27.

For this application, the apparatus comprises a centrifuge 45 to which the liquid recovered in the tank 43 is delivered and already purified by decantation, a chamber 46 for pressurizing the liquids purified by centrifugation, and filtration means 47 to which the liquids are injected under pressure.

As the filtration process, ultrafiltration, tangential filtration or osmotic filtration may be utilized.

The apparatus comprises further a ventilator fan 48 intended to reduce the pressure in the enclosure which constitutes the water closet, and two filters, a bacteriological filter 49 and an activated carbon filter 50 are arranged at the discharge of the fan 48.

Such an apparatus, of low weight and size, permits recovery of solid excrement and other solid material (paper . . . ) on the storage spool 39, and directly rejects liquid excrement after treatment, or reuse the latter, particularly for washing ones hands.

I claim:

1. A device for the recovery of waste material characterized in that it comprises in combination:

a receptacle (9; 62) provided with an opening (10; 63) for the introduction of waste, a sheath (19) arranged around the receptacle (9; 62) on the exterior thereof and invaginating to the interior of said receptacle across the opening (10; 63), said sheath having a cross-section smaller than that of the receptacle (9) and being adapted to expand radially, an obstruction for changing direction (9a; 66, 67) arranged downstream of the introduction opening (10; 63), transversely with respect to the sheath (19), said obstruction being arranged in order to be located in the path of said sheath so as to incurve the trajectory thereof, means (26–32, 34–37; 73–82, 86–90) for carrying away the sheath (19) adapted to cooperate with a portion thereof downstream of said obstruction for changing direction, and for:

maintaining constantly under tension the portion of the sheath (19) situated upstream of said carrying away means for causing a closure of said sheath upon contact with the direction changing obstruction (9a; 66, 67), causing on command a displacement of the entire sheath so as to cause a new portion of the sheath to enter into the receptacle (9; 62), means for actuating the carrying away means, and a storage zone for the sheath (19) arranged downstream of the moving means (26–32, 34–37; 73–82, 86–90).

2. A device as in claim 1, characterized in that the receptacle (9; 62) has a tubular cross-section of increasing width in the direction of the introduction opening (10; 63).

3. A for the recovery of waste material characterized in that it comprises:

a receptacle (9; 62) provided with an opening (10; 63) for the introduction of waste, a sheath (19) arranged around the receptacle (9; 62) on the exterior thereof and invaginating to the interior of said receptacle across the opening (10; 63), said sheath having a cross-section smaller than that of the receptacle (9) and being adapted to expand radially, an obstruction for changing direction (9a; 66, 67) arranged downstream of the introduction opening (10; 63), transversely with respect to the sheath (19), said obstruction being arranged in order to be located in the path of said sheath so as to incurve the trajectory thereof, means (26–32, 34–37; 73–82, 86–90) for carrying away the sheath (19) adapted to cooperate with a portion thereof downstream of said obstruction for changing direction, and for:

maintaining constantly under tension the portion of the sheath (19) situated upstream of said carrying away means for causing a closure of said sheath upon contact with the direction changing obstruction (9a; 66. 67), causing on command a displacement of the entire sheath so as to cause a new portion of the sheath to enter into the receptacle (9; 62), means for actuating the carrying away means, and a storage zone for the sheath (19) arranged downstream of the moving means (26–32, 34–37; 73–82, 86–90), a reel (20; 71) of a tubular cross-section arranged between the obstruction for changing direction (9a; 66, 67) and the moving means (26–32, 34–37; 73–82, 86–90), and arranged so that the sheath (19) passes to the interior of the reel, a second sealed sheath stored around the reel (20; 71) on the exterior of the latter and adapted to be unreeled around the first sheath (19), in such a manner as to encase the latter and to be pulled therewith by the carrying away means (26–32, 34–37; 73–82, 86–90).

4. A device as in claim 3 characterized in that the obstruction for changing direction comprises an elbow (9a) arranged in the extension of the opening (10) and arranged such that the sheath (19) recloses itself upon contact with the upper portion of said elbow.

5. A device as claim 1, characterized in that the obstruction for changing direction is comprised of two parallel axles (66, 67), called upstream and downstream, arranged transversely at a distance from each other so that at the time the sheath passes between said axles, the path of the latter is recurved in such a manner that said sheath recloses itself upon contact with the downstream axle (67).

6. A device as in claim 4, characterized in that the carrying away means comprises:

pulling means (26–32, 34–37) adapted to cause a displacement of the sheath (19) over a predetermined distance, in such a manner as to cause a new portion of the sheath to penetrate into the receptacle (9), storing means situated in storage zone and comprising a take-up reel (39) mounted on a rotation shaft (40), and means (42) for causing rotation said take-up reel for causing it to rotate an angular distance equivalent to a linear distance of displacement of the sheath (19), during each actuation of the pulling means.

7. A device as in claim 6, characterized in that the pulling means comprises:

two transverse rolls (26, 27) arranged in such a manner as to be position on opposite sides of the sheath (19), said rolls being secured at each of their ends to an axle (28) eccentric with respect to their longitudinal axis of symmetry, driving means (32) for said rolls (26, 27) controlled by the actuating means (33) and able to displace the assembly of said rolls along the sheath (19) between an upstream and a downstream position, return means (34) able to return the rolls (26, 27) from their downstream position to their upstream position, means (35–37) for pivoting the axles (28) of the rolls (26, 27) for maintaining said rolls:

in contact with each other during their displacement from their upstream position to their downstream position so as to move the sheath (19) pinched between the rolls, spaced from each other during their return from their downstream position to their upstream position.

8. A device as in claim 7, characterized in that:

the pivoting means comprises for each roll (26, 27) a lever (35) secured to the axle (28) of said roll, and upstream (37) and downstream (38) stop members adapted to cause rotation of said lever, bistable elastic means (38) associated with the levers (35) and arranged to hold the rolls (26, 27) in one or the other of their relative positions, after pivoting of said levers.

9. A device as in claim 7, characterized in that the means for causing rotation of the reel (39) comprises a spring motor (42) prestressed in a preliminary step, and adapted to cause a rotation of said reel when the rolls (26, 27) are in their spaced apart position.

10. A device as in claim 6 taken together, characterized in that it comprises a housing (8) provided with an opening on an upper face, and adapted to house the receptacle (9), the pulling means (26–32, 34–37) and the storage means (39), said receptacle and storage means being mounted in a removable manner on the interior of said housing.

11. A device as in claim 10, characterized in that:

the receptacle (9) comprises two transverse axles (11, 12) fixed externally above and below said receptacle near its end opposite the opening for introducing waste (10), the housing (8) comprising four slides (13, 17) arranged to slidingly receive the axles (11, 12) of the receptacle (9), and provided near their end with blocking members (14, 18) for blocking said axles against translation.

12. A device as in claim 1, characterized in that:
the sealed sheath (25) is stored around the reel (20) in such a manner as to be invaginated on the interior of said reel around the first sheath (19),
the reel (20) is adapted to be housed over its greatest length in the receptacle (9), downstream of the elbow, and comprises two transverse axles (21, 22) fixed externally above and below said reel, at one of the ends thereof, said axles, having a length less than the axles (11, 12) of the receptacle (9) being supported at their ends by a removable piece (23, 24) for connecting with an axle (11, 12) of the receptacle (9).

13. A device according to claim 10, characterized in that the housing (8) comprises two grooves (41) inclined with respect to the vertical for housing the ends of the rotational shaft (40) of the reel (39).

14. A device as in one claim 1, characterized in that it comprises a cart (1–3) able to support the housing (8), provided with a removable cowling (6) pierced by an opening (7) conjugate with the opening (10) for introduction into the receptacle (9).

15. A device as in claim 14, characterized in that it comprises aspiration means adapted to create a depressed pressure on the interior of the housing, and filtration means for the air discharged by the aspiration means.

16. A device as in one of claim 5, characterized in that the means for carrying away said sheath (19) comprises:

two transverse rolls (73, 74)) each carried by a rotational shaft (75, 76) arranged on opposite sides of the sheath (19) such that it is maintained pinched between said rolls, means for causing rotation of said rolls (73, 74) controlled by the actuating means (54), adapted upon each command to cause the rotation of said rolls in a unidirectional manner and in opposite directions, a predetermined angular distance, flip-flop means (77) for the rotational shaft (76) of at least one of the rolls (74), able to permit the rolls (73, 74) to separate from each other, return means (78) connecting the rotational shafts (75, 76) of the rolls (73, 74) in such a manner as to exert a force tending to keep the latter in contact with each other.

17. A device as in claim 16, characterized in that the rolls (73, 74) comprise a peripheral face having channels extending along the generatrices thereof.

18. A device as in claim 16, characterized in that:
the rotational shaft (75) of one of the rolls (73), called fixed, is mounted fixed in translation, the shaft (76) of the other roll (74), called movable, being secured to levers (77) able to permit a rocking of said movable roll with respect to the fixed roll (73),
the means for causing rotation of the rolls comprising means (79-82, 86) for unidirectionally rotating the fixed roll, associated with actuating means (54), and transmission members (87-90) able to transmit this rotational movement, in a reverse direction, to the movable roll.

19. A device as in claim 18, characterized in that the transmission members comprise:
a double groove pulley (87) mounted in a coaxial manner with respect to the axis of rotation of the levers (77),
two pulleys (88), each secured to rotational shaft of one of the rolls (73, 74),
two drive belts (89, 90) connecting each pulley (88) of one of the rolls (73, 74) to the double groove pulley (87), and arranged in such a manner as to reverse the direction of rotation of the movable roll (74) with respect to that of the fixed roll (73).

20. A device as in claim 16, characterized in that the receptacle (62), the driving means (73–82, 86–90) for the sheath (19) and the storage zone are arranged one above the other.

21. A device as in claim 20, characterized in that it comprises a shell (55) provided with an upper opening (58), adapted to house the receptacle (62) and the moving means (73–82, 86–90), and to define in the lower part an accessible storage zone, the receptacle (62) being mounted in a removable manner in said shell.

22. A device as in claim 21, characterized in that:
the sealed sheath (25) is stored around the reel (71) in such a manner as to unreel itself in the lower extension of said reel, around the first sheath (19) leaving the latter,
the reel (71) has an upper flange (72) arranged to permit suspending said reel on the interior of the shell (55) provided for that purpose with support elements (91) for said flange,
the receptacle (62) is arranged to come to rest on the flange (72) of the reel (71).

23. A device as in claim 22, characterized in that the reel (71) has a rectangular tubular cross-section, and comprises two lateral faces (71a) having longitudinally a concave shape.

24. A device as in claim 20, characterized in that:
the receptacle (62) has a tubular oval cross-section and comprises an upper portion (62a) of a cross-section increasing in the direction of the introduction opening (63), and a lower portion (62b) of a constant cross-section,
the axles (66, 67) extending along the greatest dimension of the receptacle (62), the upstream axle (66) being arranged in the upper portion (62a) of said receptacle, and the downstream axle (67) being arranged in the lower portion (62b) and being connected to the upstream axle (66) in such a manner as to be able to rock relative to the latter.

25. A device as in claim 24, characterized in that the upstream axle (66) is covered by a tube (68), the downstream axle (67) resting in the core of a U the ends of which the ends of the flanges (69) are secured to said tube.

26. A device as in claim 1, characterized in that it comprises a pump (51) able to be controlled by the actuating means (33) and provided with a suction inlet connected to a reservoir (52) for containing an antiseptic product, and a pressure outlet connected to an injector (53) arranged in said receptacle (9).

27. A device as in claim 4, intended to serve as a water closet, characterized in that:
the receptacle (9) is shaped in the downstream elbow in such a manner as to comprise a tank (43) for recovery of liquid, provided with an evacuation outlet for said liquid, the first sheath (19) having a texture adapted to allow liquid to flow therethrough into the recovery tank (43), treating means (45–47) adapted to assure the treatment of recovered liquid in order to permit its discharge or its reuse.

28. A device as in claim 27, characterized in that the treating means comprises means (45) for centrifugation of liquids, means (46) for pressurizing the recovered liquids after centrifugation, and means (47) for filtration to which the liquid is delivered under pressure.

29. A device as in claim 28, characterized in that it is housed in an enclosure comprising aspiration means (48) for creating a reduced pressure on the interior of said enclosure, and means (49, 50) for filtration of the air discharged by the aspiration means.

\* \* \* \* \*

UNITED STATES PATENT AND TRADEMARK OFFICE
CERTIFICATE OF CORRECTION

PATENT NO. : 5,884,346
DATED : March 23, 1999
INVENTOR(S) : Patrick Hengl

It is certified that error appears in the above-identified patent and that said Letters Patent is hereby corrected as shown below:

On the title page, item [22], "Nov. 13, 1993" should read --Nov. 10, 1993--.

Signed and Sealed this

Thirty-first Day of August, 1999

Attest:

Q. TODD DICKINSON

*Attesting Officer*    Acting Commissioner of Patents and Trademarks